US006419941B1

(12) United States Patent
Farone et al.

(10) Patent No.: US 6,419,941 B1
(45) Date of Patent: Jul. 16, 2002

(54) POLYOL ESTER INSECTICIDES AND METHOD OF SYNTHESIS

(75) Inventors: William A. Farone, Irvine; Tracy Palmer, Rancho Santa Margarita; Gary Joseph Puterka, Sheperdstown, all of CA (US)

(73) Assignee: AVA Chemical Ventures L.L.C., Portsmouth, NH (US)

( * ) Notice: Subject to any disclaimer, the term of this patent is extended or adjusted under 35 U.S.C. 154(b) by 0 days.

(21) Appl. No.: 09/504,016

(22) Filed: Feb. 18, 2000

(51) Int. Cl.$^7$ ................................................ A01N 25/02
(52) U.S. Cl. ...................... 424/405; 424/406; 514/25; 514/53; 514/546; 514/549
(58) Field of Search .................. 424/405; 514/25, 514/53, 738, 546, 552, 547, 549

(56) References Cited

U.S. PATENT DOCUMENTS 5,756,716 A    5/1998   Farone ........................ 536/120

OTHER PUBLICATIONS

Puterka er al., *J. Econ. Entomol.* 88(3), 615–619 (1995).
Thurston et al., *Ent. exp. & appl.* 5, 233–238 (1962).
Parr et al., *J. Econ. Entomol.* 61(6), 1525–1531 (1968).
Siegler et al., *J. Econ. Entomol.* 18, 292–299 (1925).
Chortyk et al., *J. Agric. Food Chem.* 44, 1551–1557 (1996).
Neal et al., *J. Econ. Entomol.* 87(6), 1600–1607 (1994).
Thurston, *J. Econ. Entomol.* 63(1), 272–274 (1970).
Imai et al., *Appl. Entomol. Zool.* 29(3), 389–393 (1994).
Adamson, *Physical Chemistry of Surfaces* 3$^{rd}$ Ed., 504–507 (1976).

*Primary Examiner*—Neil S. Levy
(74) *Attorney, Agent, or Firm*—Cynthia H. O'Donohue

(57) ABSTRACT

The present invention relates to an environmentally acceptable synthesis method of polyol esters that produces no toxic by-products methods during the synthesis. The present invention also provides for the use of these esters as safe and effective insecticides.

1 Claim, 12 Drawing Sheets

POLYOL ESTER INSECTICIDES AND METHOD OF SYNTHESIS

STATEMENT REGARDING FEDERALLY SPONSORED RESEARCH AND DEVELOPMENT

The U.S. Government has a paid-up license in this invention and the right in limited circumstances to require the patent owner to license others on reasonable terms as provided for by the terms of Grant 99-33610-7466 awarded by U.S. Department of Agriculture.

FIELD OF THE INVENTION

The present invention relates to methods of synthesis of polyol ester insecticides. More particularly, this invention concerns a method of synthesis of sugar esters which ensures that the resulting ester's chemical structure has insecticidal activity.

BACKGROUND OF THE INVENTION

Sucrose octanoate has proven to be a useful insecticide compound. Varieties of sucrose esters are contained in the natural wax of leaves. Discussions of these esters may be found, for example, in Neal, J. W. Jr. et al, J. Econ. Entomol. 87, 1600–1607(1994); Puterka, G. J., et al, J. Econ. Entomol. 88, 615–619(1995), and Lui, T. X. et al, J. Econ. Entomol. 89, 1233–1239 (1996). Sucrose octanoate is contained in the mixture of sucrose esters made when coconut fatty acids are used to make sucrose esters. The sucrose esters are readily biodegradable and hydrolyze to readily metabolizable sucrose and fatty acid. Sucrose esters can be made by the methods disclosed in U.S. Pat. No. 5,756,716, William A. Farone and Robert Serfass, "Method for Production of Sugar Esters", May 26, 1998. Other methods for making these compounds are also known and referenced in this patent.

The efficient production of sucrose octanoate involves several steps, including an esterification, a transesterification and then a purification step. It would be extremely useful to have compounds with similar insecticidal activity, similar environmental acceptability, made from similar natural products, that could be synthesized in fewer steps. Unfortunately there is no means of predicting the chemical structures that will have insecticidal activity. There is no general agreement as to exactly how the sugar ester compounds obtain their insecticidal activity.

One hypothesis is that the compounds like sucrose laurate or sucrose octanoate act as surfactants to dewax the insect's protective coating. The insect then either dehydrates or is readily attacked by microbes. This hypothesis is supported by the observation that the compounds are "contact" insecticides. Since the sucrose esters are constituents of plant leaves, there is another hypothesis that the compounds somehow interfere with the metabolism of the insect to prevent them from eating the tissue that the esters protect. This hypothesis requires ingestion of the material by the insect and cannot be ruled out since "contact" can also result in ingestion.

It is also known that the short chain sucrose esters that are effective as insecticides have certain properties that seem to enhance that activity. Chortyk and co-workers at the United States Department of Agriculture [see Chortyk, O. T., Pomonis, J. G., and Johnson, A. W., J. Agric. Food Chem., 44, 1551–1557 (1996)] concluded that the sucrose esters with fatty acid chain lengths below 12 were more effective especially when there were 2 or 3 side chains on the sucrose.

The fact that there are eight hydroxyl groups that can be esterified in sucrose means that, in principal, one can make 8 sucrose monoester, 28 diester and 56 triester isomers. It is unpredictable if all esters of one type (e.g. monoesters, diesters, etc.) are equally effective. Molecular orbital calculations performed in the inventors' laboratory suggest that not all esters are equally likely to be produced during synthesis.

SUMMARY OF THE INVENTION

In one aspect the present invention relates to a new environmentally friendly method of synthesis of polyol esters. The inventors found that the synthesis method is important in defining the distribution of isomers in complex molecules with the subsequent result that one must either specify the exact nature of the isomers involved and/or the method of synthesis as a mean of selecting the best insecticides.

More particularly another aspect of this instant invention is the use of these esters as safe effective insecticides. The inventors found the surprising and unexpected result that octanoic acid (C8) sorbitol esters are more effective as insecticides, and that the decanoic acid (C10) acid esters are the most effective for xylitol.

Also there was an unexpected finding that for sucrose octanoate the monoesters were more effective as insecticides than the diesters and triesters. This finding is in contradiction to the finding of Chortyk who concluded that sucrose esters with fatty acid chain lengths below 12 were more effective especially when there were 2 or 3 side chains on the sucrose. Additionally Chortyk synthesized his esters through the use of a multi-step process using acid chlorides which generated hazardous by-products. His method of synthesis generated primarily diesters and triesters while the method of U.S. Pat. No. 5,756,716 optimally can generate a high percentage of monoester.

DETAILED DESCRIPTION OF THE INVENTION

The method of preparation of the polyol esters, in particular sorbitol and xylitol, of this invention is best explained in terms of 7 steps. One of the objects of the preparation method is have an environmentally acceptable synthesis that produces no toxic by-products. Another object is to develop a method that allows the entire range of esters to be prepared using essentially the same procedure thus allowing mixed esters to be produced or the same production facility to be used to make esters that could be targeted against specific insects. Without limiting the scope of this invention as expressed by the claims which follow, the synthesis steps will be discussed briefly.

The process is basically as follows:

1. The desired organic acid (e.g. octanoic, deconoic, but not limited to these) is charged to the reactor at a temperature sufficiently high to keep it in liquid form.
2. The polyol (e.g. either xylitol or sorbitol) is added in an amount that would allow the production of the monoester stoichiometrically plus an additional 10% to drive the reaction essentially to completion.
3. An esterification catalyst is added. Any usual catalyst can be used such as sulfuric acid or phosphoric acid. Phosphoric acid is the preferred embodiment in this case since neutralization at the completion of the reaction provides a phosphate salt that can either be left in the product (since phosphorous is an essential plant nutrient and phosphates are a known method of providing phosphorus) or removed by filtration if desired (whereupon the salt can be sold separately for fertilizer use).

4. The reactor is held at a temperature sufficiently high along with a pressure sufficiently low to allow water to be removed as the esterification reaction proceeds. For most of the esters a temperature around 150° C. and atmospheric pressure was used.

5. The reaction is allowed to proceed until the remaining organic acid reaches a low equilibrium value. This point can be determined very simply by monitoring the free acid content of the reaction mixture and comparing differing reaction times (see Example 1 and 2). When the free organic acid is reduced no further the reaction is essentially completed. The equilibrium value in weight percent depends on the molecular weight of the organic acid and the structure of the isomers formed. Once determined for a particular organic acid and polyol combination it can be used as a measure of reaction completion.

6. At the completion of the reaction (approximately 18–30 hours for the esters synthesized for the insecticidal studies) the solution is neutralized with an amount of base that is sufficient to neutralize all of the mineral acid used as a catalyst plus bring the solution to a desired pH for subsequent use. If calcium hydroxide is used as the base, calcium phosphate can be filtered out of the product. Other bases could be used depending on the desired nature of the final product. This procedure was followed to allow for a product of good water solubility with little or no residual fine solid particles.

7. The product (filtrate from Step 6) is analyzed and is ready for use.

This procedure of this present invention is deliberately made deceptively simple. Due to the fact that the insecticide nature as well as other properties of these materials change depending on the isomers it is desired to have a simple process that can be repeated with little difficulty. The only "waste product" of the reaction is the water removed during the esterification. The equipment and reaction conditions are selected in such a manner that the tendency of any of the organic acid to distill over with the water is thwarted by the use of appropriate reflux allowing the water to be removed and the acid to fall back into the reactor. Thus, in the preferred method a distillation column (tray or packed column) is used over the reactor to insure retention of the acids.

Figure 1:
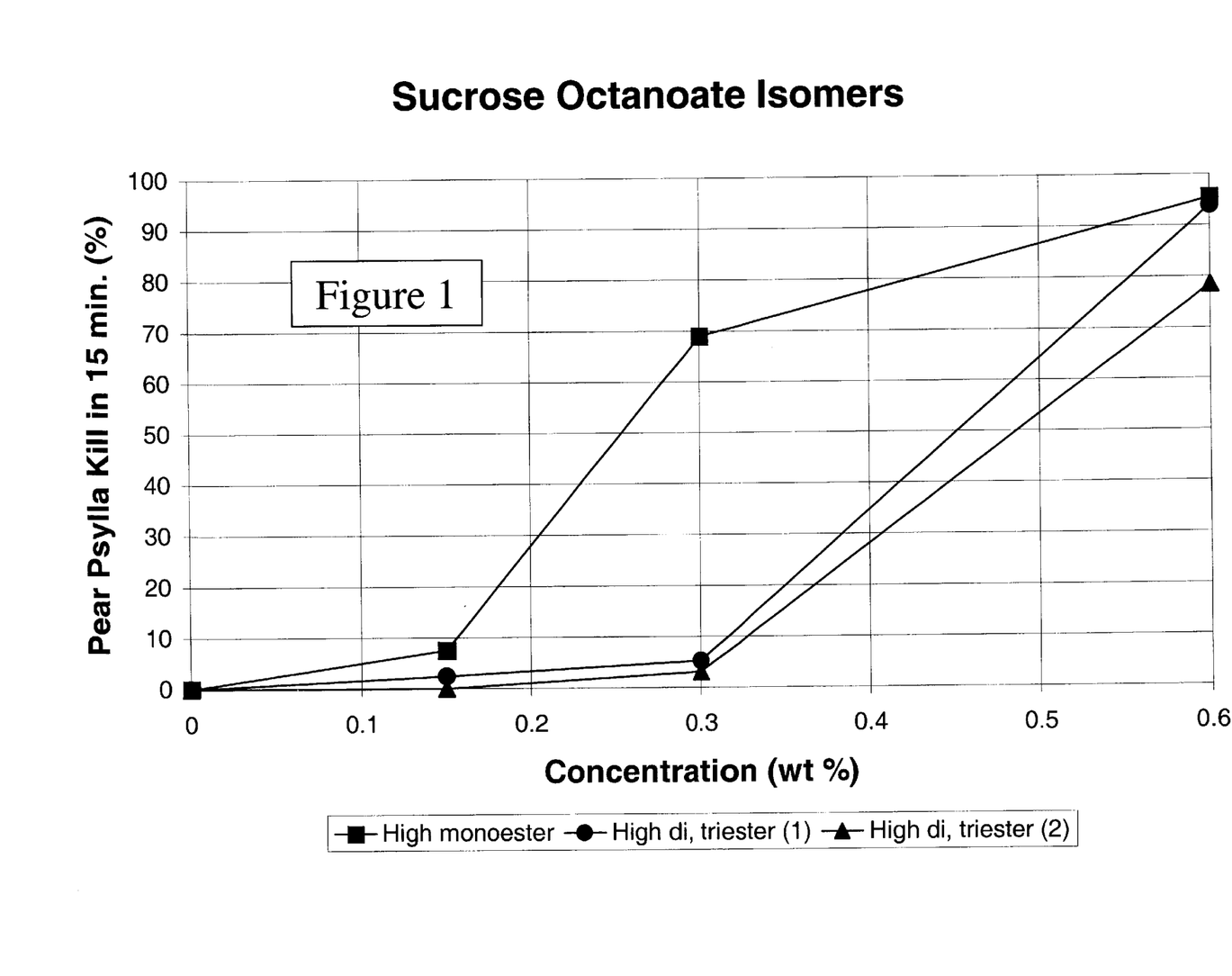

Sucrose octanoate is synthesized by the method described in U.S. Pat. No. 5,756,716, incorporated herein by reference. The resultant product, sucrose octanoate, is found to have monoesters that are more effective as insecticides than the diesters and triesters of sucrose octanoate. FIG. 1 shows the results on pear psylla for the sucrose octanoate with high monoester content prepared by the referenced method compared to the Chortyk esters, the high di and triesters. This finding is in contradiction to the finding of Chortyk. The inventors of the above described process find the method of synthesis is important in defining the distribution of isomers in complex molecules with the subsequent result that one must either specify the exact nature of the isomers involved and/or the method of synthesis as a mean of selecting the best insecticides.

Figure 2:
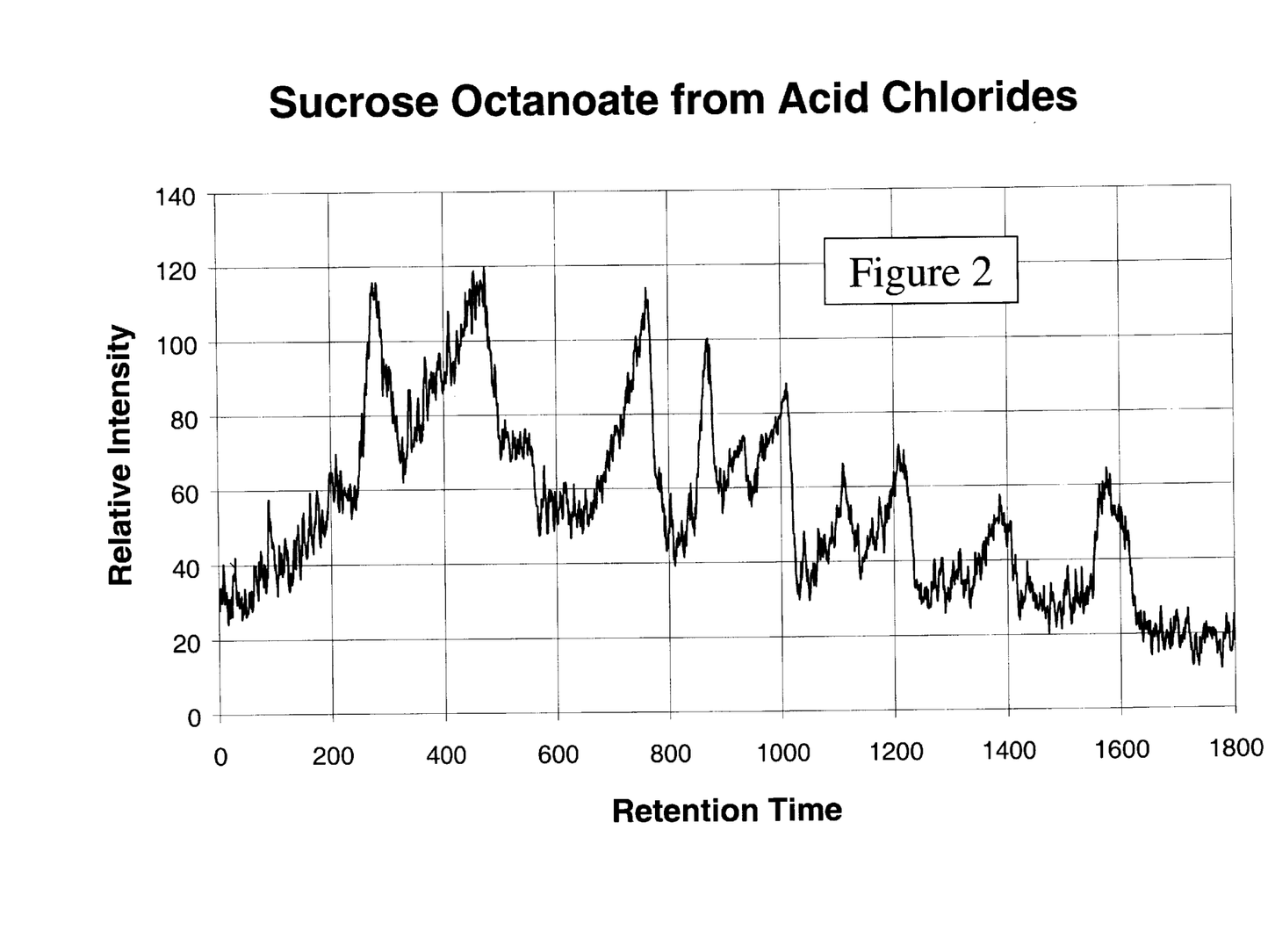
Figure 3:
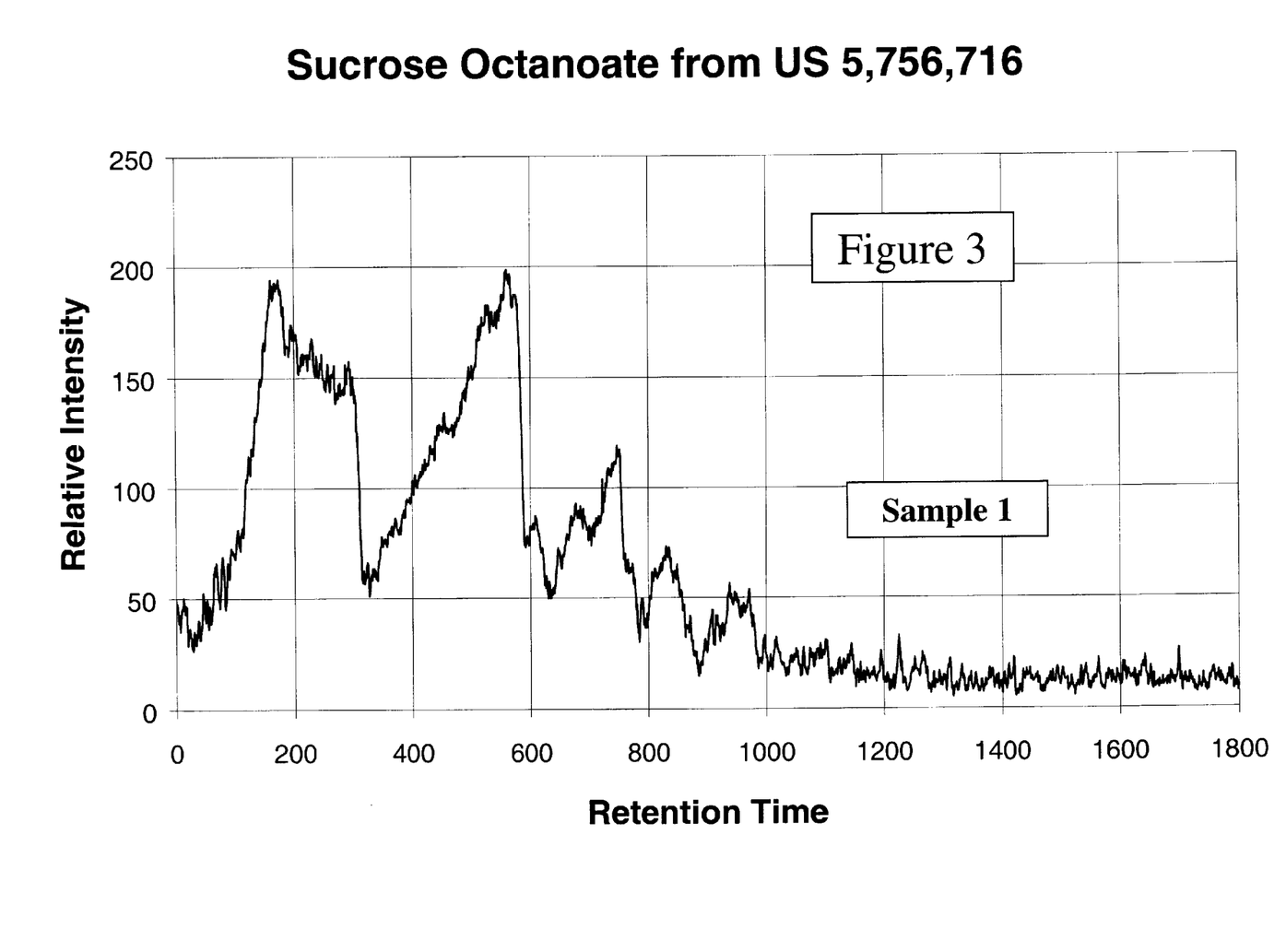
Figure 4:
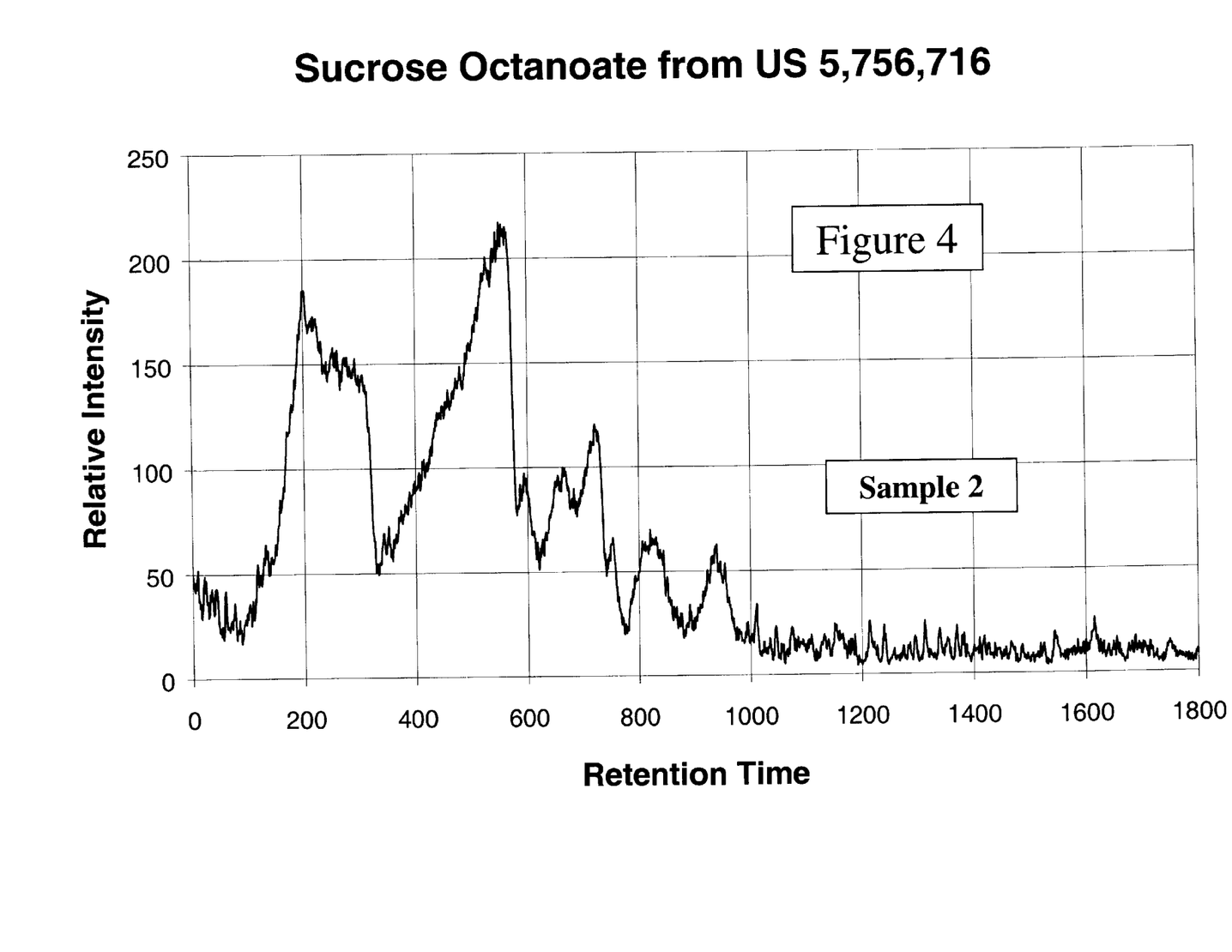
Figure 5:
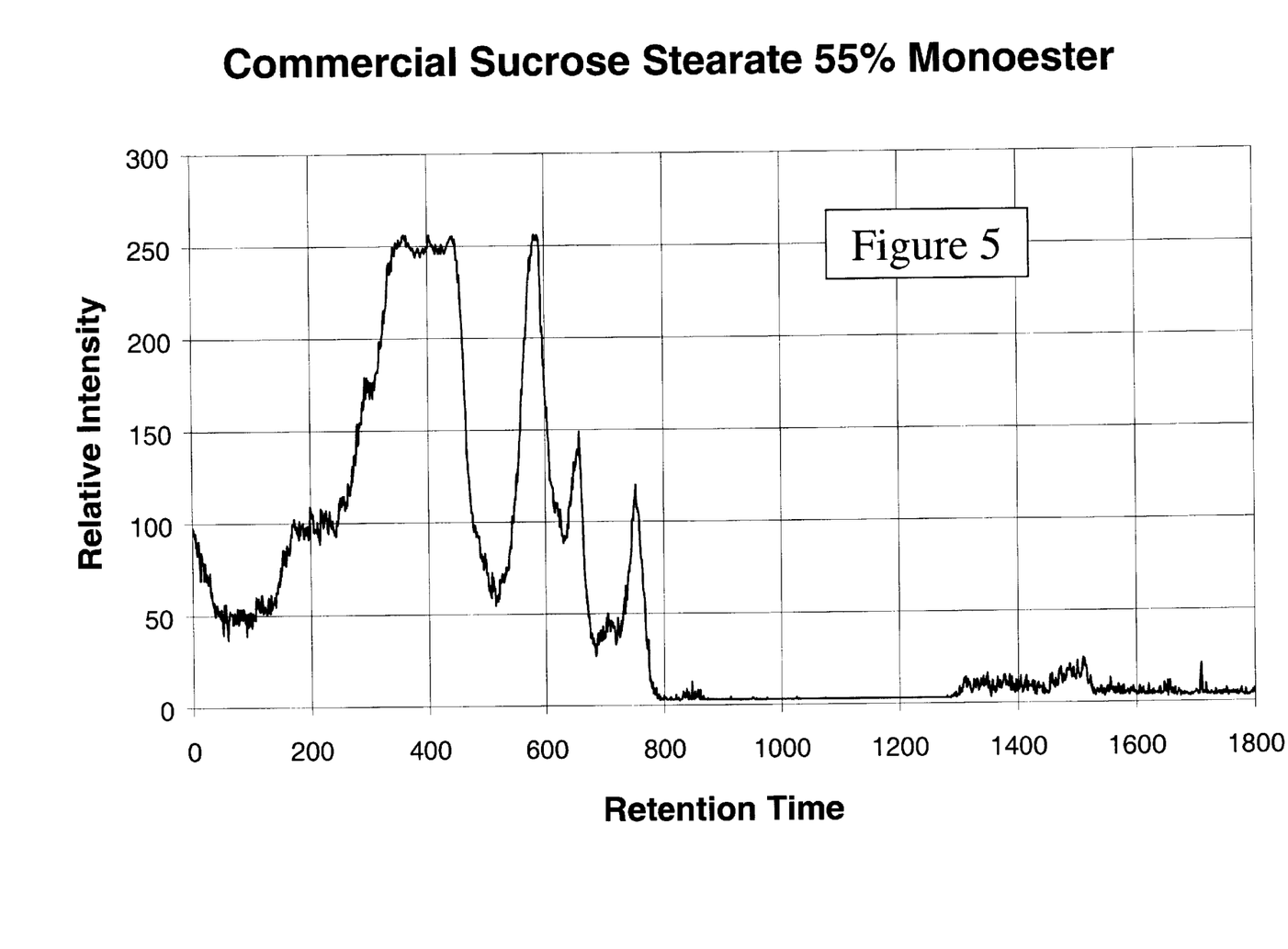

To study the chemical differences between the sucrose octanoate synthesized by Chortyk and the inventors' material, the products were subjected to thin layer chromatography under identical conditions, side by side, on the same plate. The chromatograms obtained by digitization of the plates are shown in FIGS. 2–4. A chromatogram of a commercial sucrose stearate product, obtained by the same method, is shown in FIG. 5. Although the commercial sucrose stearate product shown in FIG. 5 does not have insecticidal activity it is shown as an independent example of the nature of a product that is high in monoester. In this analytical methodology the higher the number of free hydroxyl groups in the molecule the tighter it is bound to the silica substrate. Thus the monoesters move more slowly and appear near the origin on the chromatogram while the diesters move fast and the triesters faster, thus the di- and triesters are further from the origin on the chromatogram. The result is separation of the various isomer fractions.

FIG. 2 shows a chromatogram of the esters made by Chortyk. Note that there are many peaks resulting from the higher isomers. FIGS. 3 and 4 show two different batches of sucrose octanoate made by the method of U.S. Pat. No. 5,756,716. There are fewer peaks with lesser area than the same sucrose octanoate ester made by the acid chloride route. The commercial product is shown in FIG. 5.

The thin layer chromatography technique is very reproducible as to the extent and number of "bands" that characterize the different isomers in the product. With liquid chromatography the individual isomer "peaks" tend to merge and overlap making resolution difficult. With the advent of computer scanners to convert the chromatogram into digital form, the thin layer technique rivals or exceeds liquid chromatographic techniques. The use of computer digitization is an improvement on the older densitometry techniques used with thin layer and gel chromatography.

In the sucrose studies the octanoate was found to be the approximately optimal chain length. Octanoic acid is a reasonably abundant fatty acid fraction of natural oils (e.g. coconut oil) after the oil is "split", i.e. hydrolyzed to glycerol and fatty acids. Nature prefers even chain fatty acids. Although the odd chain fatty acids are also likely to be reasonably effective it is the inventors' purpose to make the biodegradation products as natural as possible. It is well known that the long chain fatty acid esters of sucrose (e.g. sucrose stearate) are extremely mild materials with excellent surfactant properties. These materials have been used as food emulsifiers for many years.

Finding useful analogs of sucrose octanoate is a matter of trial and error. The chemical structure can be suggestive, however. The objective was to find materials that:

1. Are simpler to synthesize
2. Would have environmental fates similar to sugar and fatty acid esters
3. Would have similar insecticidal activity when used either alone or in combination.

A wide variety of compounds were synthesized. The compounds that were proven to have the best activity when compared to sucrose octanoate are sorbitol and xylitol esters of short chain fatty acids, particularly the octanoic and decanoic acid monoesters. These compounds are more easily prepared than the sucrose octanoate. They can be synthesized directly from the raw materials in a single step using only a neutralizable mineral acid as a catalyst in the process described earlier. Due to the greater ease of synthesis these materials could be less expensive even if they are slightly less effective than sucrose octanoate.

Surprisingly, there is no one chemical structure that was shown to be optimally effective for all the insects tested for the sorbitol and xylitol esters, This differs from the sucrose esters where not only is the octanoate the most effective but the distribution of isomers toward the monoesters also defines a superior insecticide. It was found that the optimum chain length for the other sugar esters differs depending on the insect species. This finding seems to support a mechanism wherein the compound is not directly toxic but rather matches some property of the insect's covering materials, i.e., provides support for the "dewaxing" hypothesis. The differing chemical make-up of the insect would be optimally matched to different "solvent" compounds.

Table 1 provides a listing of the compounds of interest. Five of them have been reported at sometime in the past and have been assigned CAS Registry numbers while three appear to be new to the literature since no CAS registry number was found.

TABLE 1

| CAS Registry Number | CA Index Name | Other Name |
|---|---|---|
| 50809-54-6 | D-Glucitol, hexanoate | Sorbitol caproate |
| 108175-15-1 | D-Glucitol, octanoate | Sorbitol octanoate |
| 108175-14-0 | D-Glucitol, decanoate | Sorbitol decanoate |
| 53637-07-3 | D-Glucitol, dodecanoate | Sorbitol laurate |
|  | Xylitol hexanaote | Xylitol caproate |
|  | Xylitol octanoate | Xylitol caprylate |
| 211876-92-5 | Xylitol decanoate |  |
|  | Xylitol dodecanoate | Xylitol laurate |

The chain lengths were systematically varied to determine if the chain length was critical as to the effectiveness as insecticides. The compounds were tested against pear psylla, tobacco hornworms, tobacco aphids and two-spotted spider mites.

Figure 6:
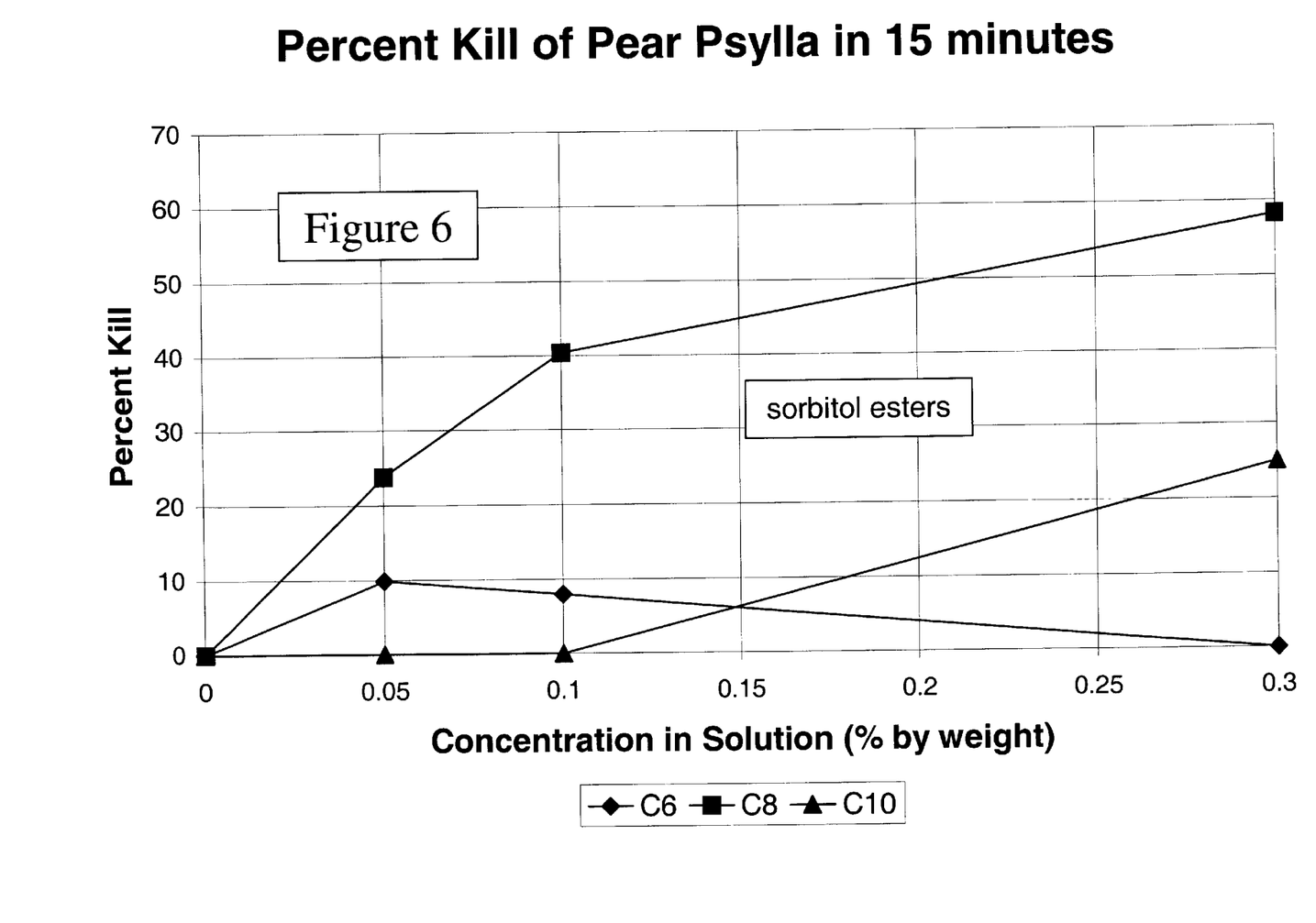
Figure 7:
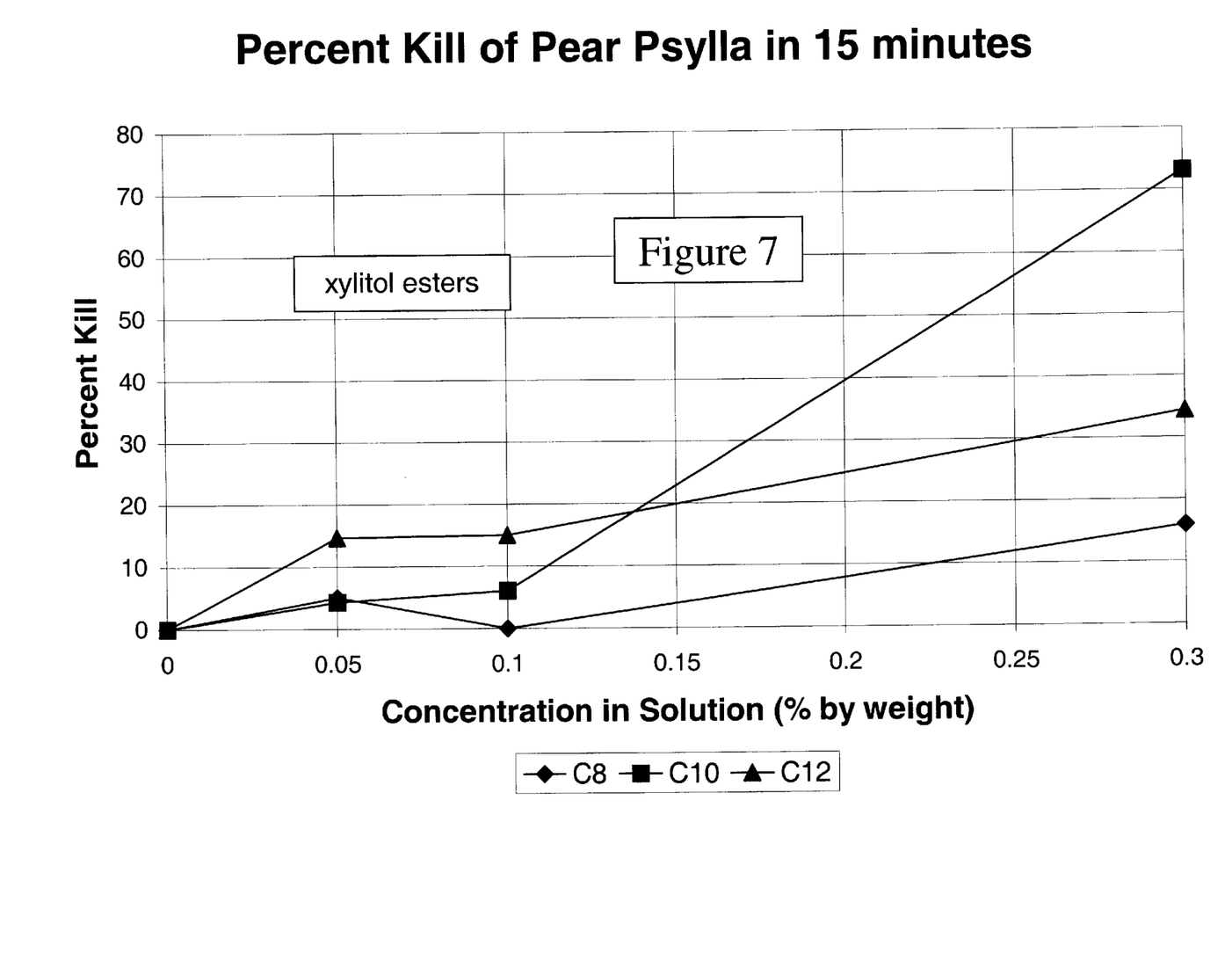

FIG. 6 shows the kill data for the sorbitol esters on pear psylla. It is clear that the C8 acid version is the most effective. For the xylitol data in FIG. 7, however it appears that the C10 acid ester is the most effective. This is a very surprising and unexpected result because the shift in the size of hydrophobic portion of the molecule for the xylitol esters has not kept in pace with the shift in the size of the hydrophilic portion of the molecule.

If the activity was explained by a simple surfactant picture, one would expect that a certain hydrophile-lipophile balance (HLB) would hold. When the size of the hydrophile decreases as it has in going from sorbitol to xylitol one would expect the size of the lipophile to also decrease to maintain the same HLB relationship. A discussion of the relationship of the molecular structure to the HLB is given by Arthur W. Adamson, "Physical Chemistry of Surfaces", Third Edition, John Wiley, 1976, pp. 505–507.

Figure 8:
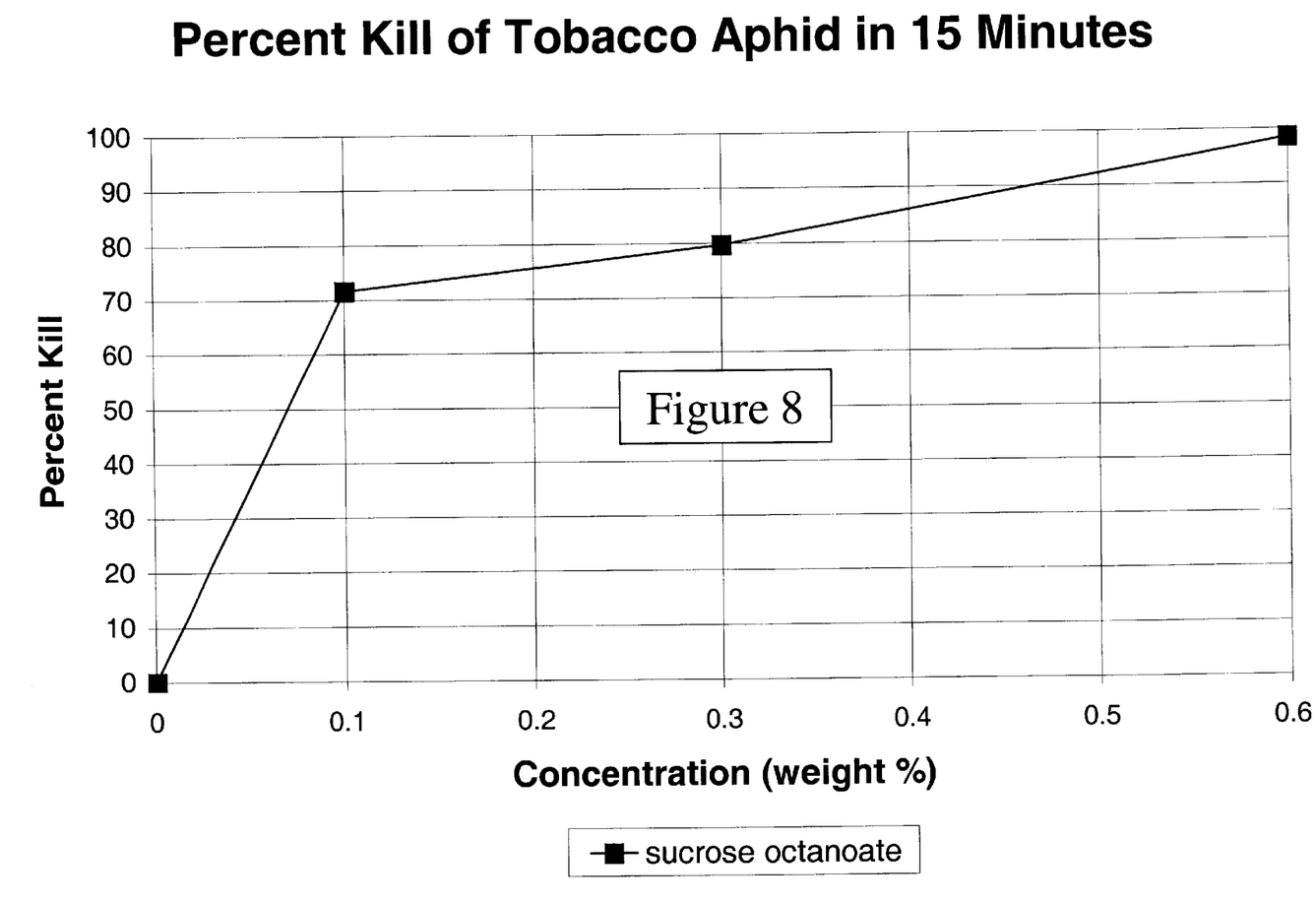
Figure 9:
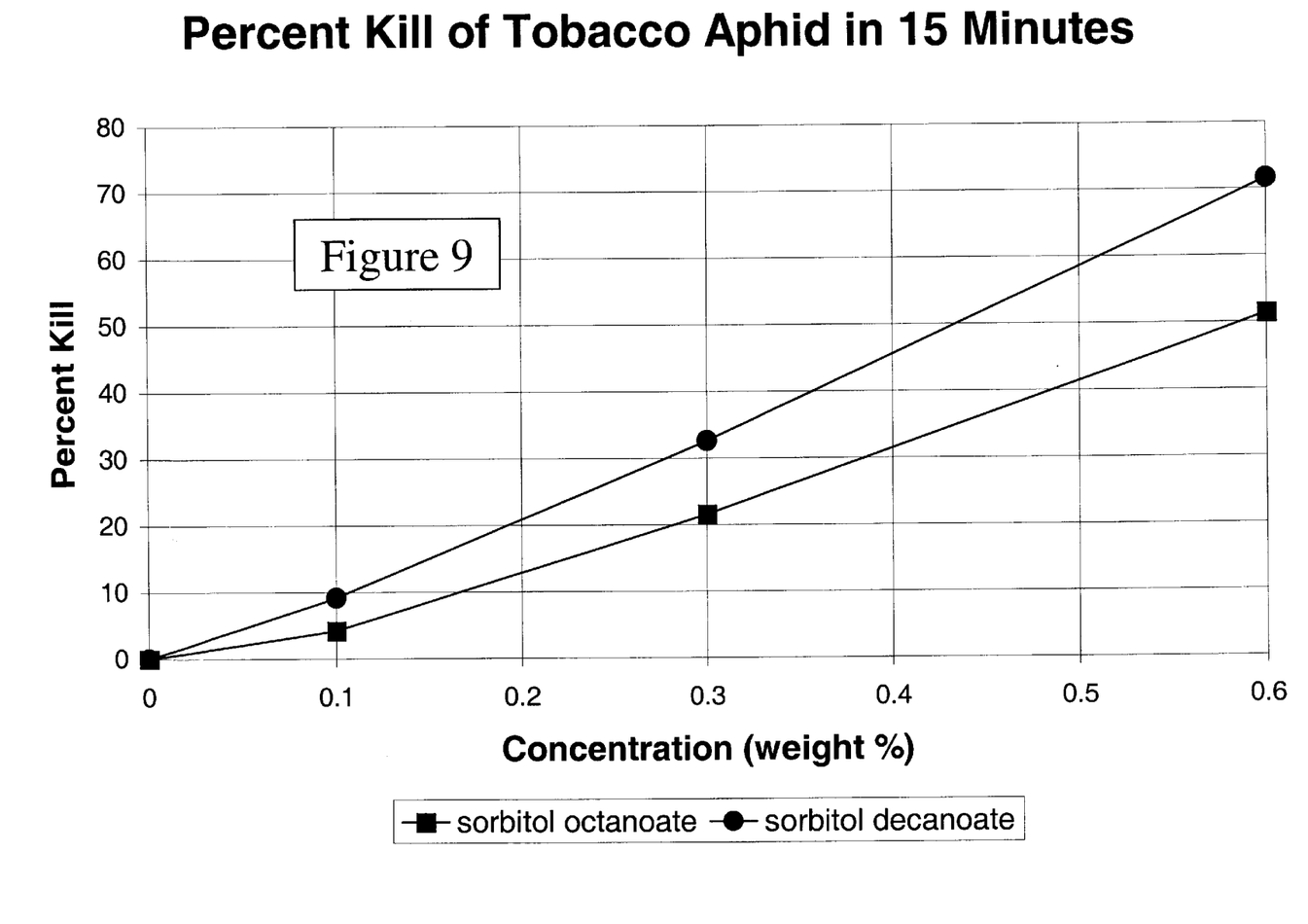

FIG. 8 shows the effectiveness of sucrose octanoate made by the methods of U.S. Pat. No. 5,756,716 against tobacco aphid. FIG. 9 shows that sorbitol octanoate is more effective than sorbitol decanoate against tobacco aphid. Note that sorbitol decanoate could still be a commercially viable product if the cost of decanoic acid was less than octanoic acid by an amount that would compensate for the increased use needed to maintain equal effectiveness. The simplicity of the method of preparation of the sorbitol and xylitol esters and the fact that the method is essentially the same for all of the sorbitol and xylitol esters makes the economic choice essentially only dependant upon the raw material costs.

Figure 10:
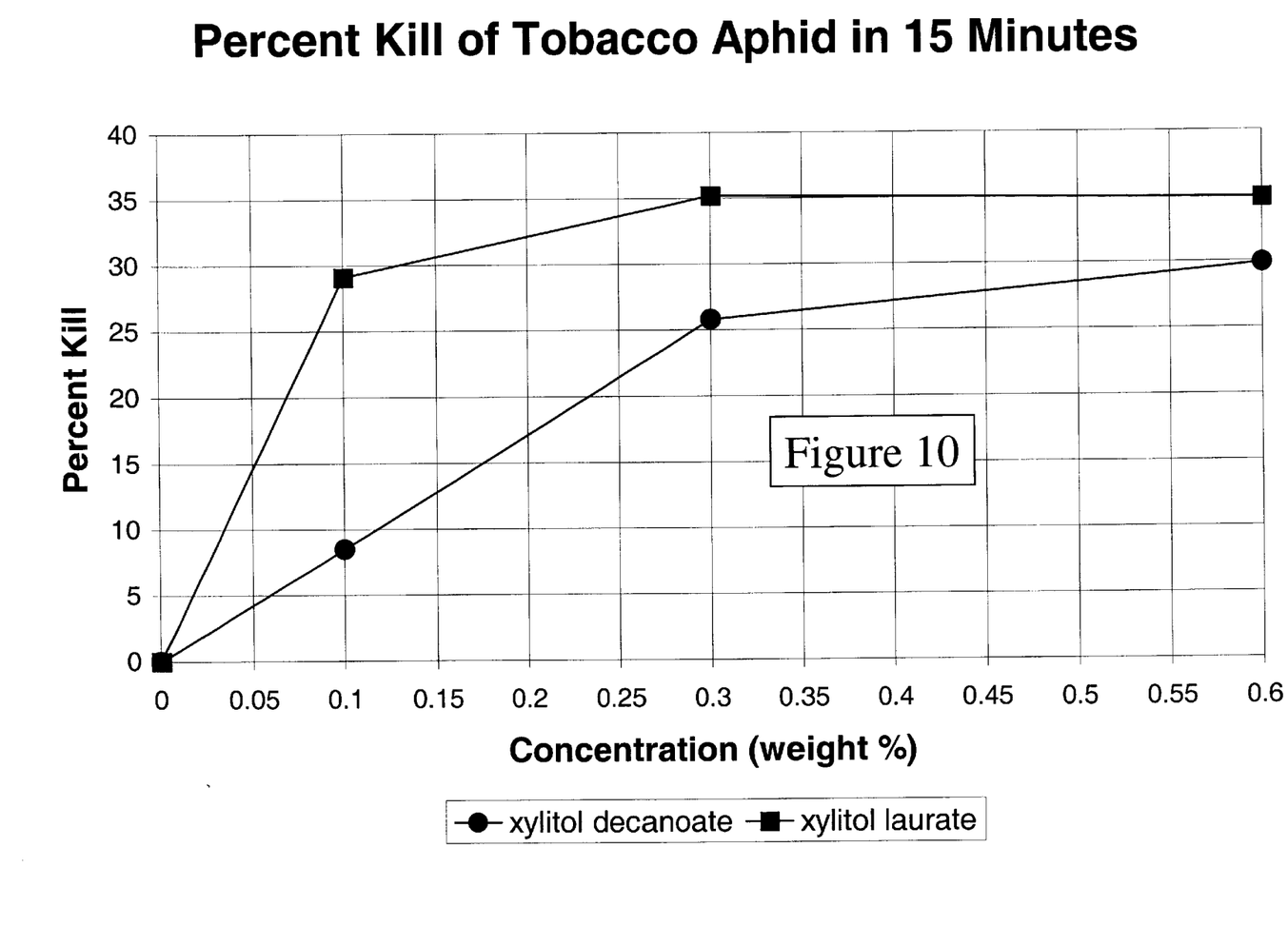

FIG. 10 shows that xylitol laurate is more effective than xylitol decanoate against the tobacco aphid. This is in contrast to the case with pear psylla where the decanoate was most effective.

Figure 11:
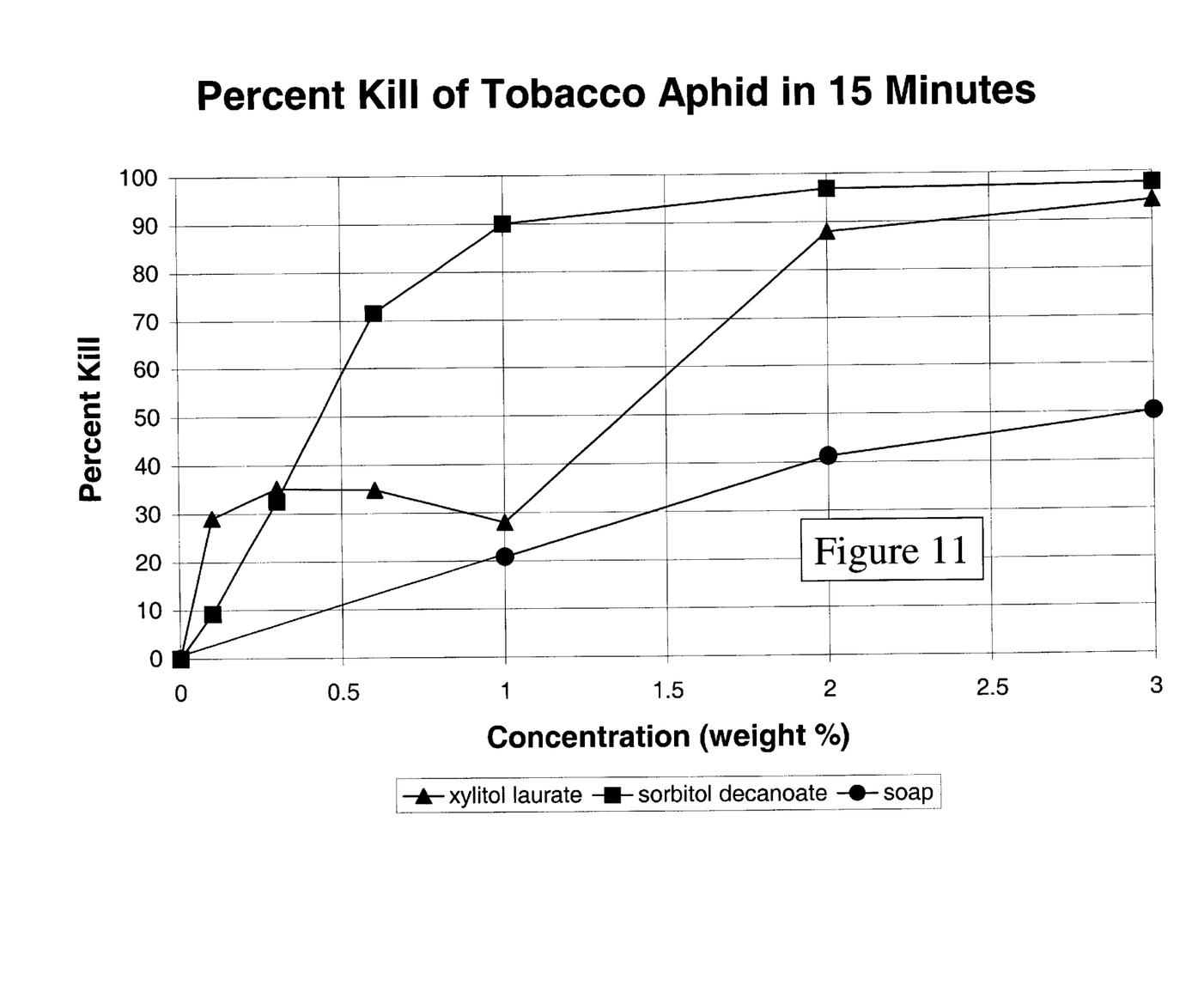
Figure 12:
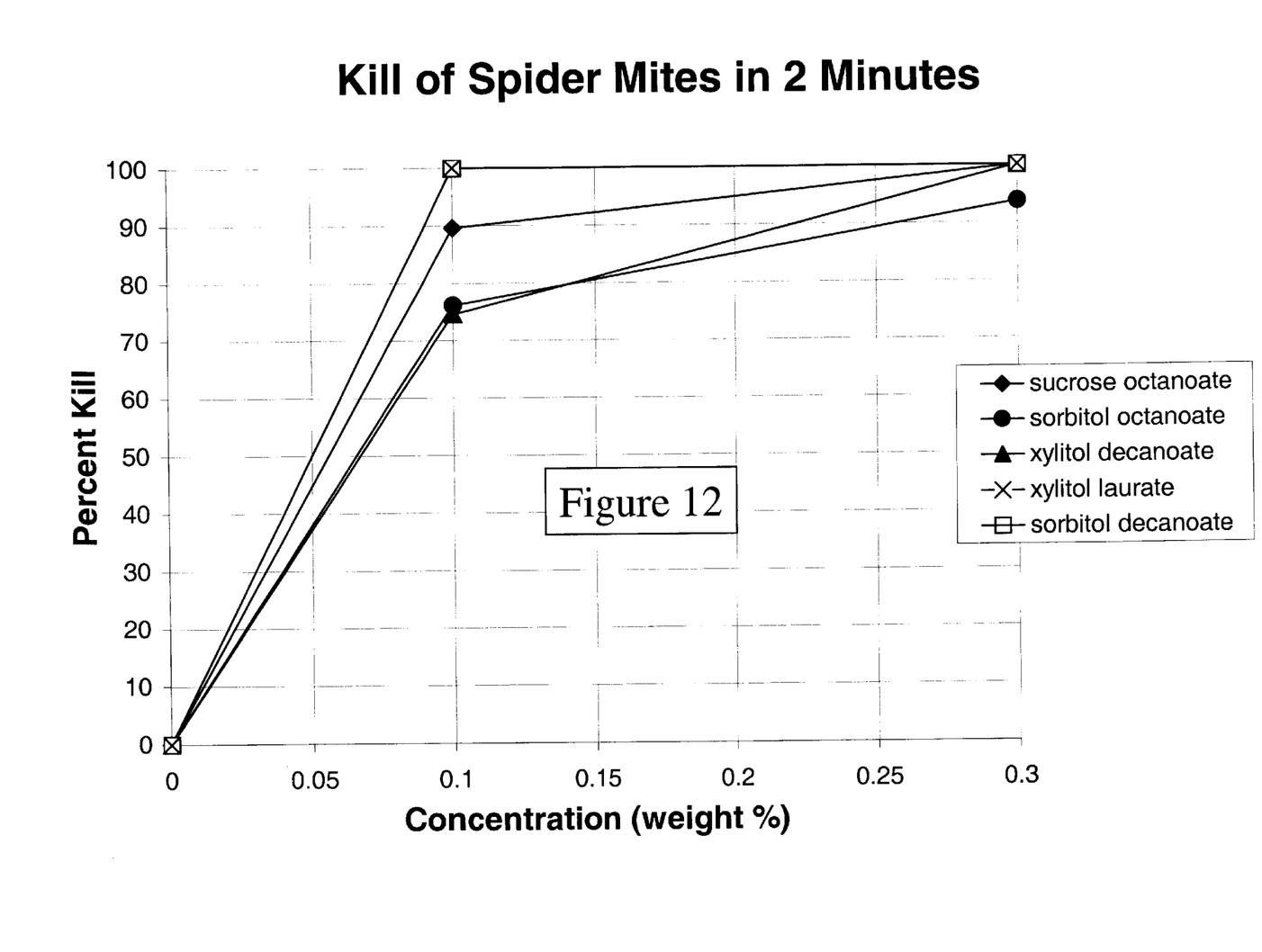

FIG. 11 shows that sorbitol decanoate is more effective than xylitol laurate against the tobacco aphid. Of greater importance, however, is the fact that both of these materials are better than a commercially available insecticidal soap product (M-Pede, Mycogen Corp., San Diego, Calif.). FIG. 12 compares several of these materials for use against the two-spotted spider mite and in this case the sorbitol decanoate is marginally more effective than the others including the sucrose octanoate.

The following are examples of making polyol esters according to the present invention. Other polyol esters as discussed above may also be made using the process of this invention.

Examples 1 and 2 were run to compare different times for the degree of conversion. This type of benchmark reaction can be performed to determine optimal conditions for other polyol esters.

EXAMPLE 1

Preparation of sorbitol octanoate: 432.44 grams of octanoic acid was put into a 2-liter round bottom, three-neck flask with a short distillation head. A mechanical stirrer was connected and 598.51 grams of sorbitol was slowly added. The catalyst in the reaction was phosphoric acid and 30.93 grams were added. A temperature controller and heating mantle were attached and the temperature of the reaction was set at 150° C. The reaction was stopped after 21 hours. The phosphoric was neutralized with 26.02 grams of calcium hydroxide. The solution was filtered to remove the calcium phosphate precipitate. The density of the product was 1.4 g/cc and the free acid was 6.40%. The degree of reaction completion was thus about 85.5%

EXAMPLE 2

Preparation of sorbitol octanoate again. 438.52 grams of octanoic acid, 600.10 grams of sorbitol and 32.122 grams of phosphoric acid was placed into a round bottom flask with a mechanical stirrer and short distillation head attached. The temperature was set at 150° C. The reaction proceeded until the free acid value was 3.88%. Total reaction time was 28 hours. The phosphoric acid was neutralized with 27.015 grams of calcium hydroxide. The product was analyzed and the density was 1.4 g/cc and the ash was 2.33%. The degree of reaction is thus 91.3%

EXAMPLE 3

Preparation of xylitol octanoate: 417.0 grams of octanoic acid was poured into a 2-liter round bottom flask with a short distillation head. A mechanical stirrer and short distillation head were attached and a heating mantle and a temperature controller was used to maintain temperature at approximately 150° C. 462.48 grams of xylitol was added slowly along with 32.422 grams of 75% phosphoric acid.

EXAMPLE 4

Sorbitol caproate was prepared by adding 348.48 grams of caproic acid and 546.51 grams of sorbitol to a 2-liter round bottom flask with a mechanical stirrer, heating mantle and temperature controller. Phosphoric acid was used as the catalyst and 39.12 grams of 75% phosphoric acid was added to the reaction. The temperature was set for 150° C. and the pressure was atmospheric pressure. The total reaction time was 24 hours. After 24 hours the phosphoric acid was neutralized with 32.90 grams of calcium hydroxide. The solution was filtered to remove the calcium phosphate precipitate. The final product was analyzed and the free acid remaining in the product was 3.97%, the density was 1.8 g/cc and the ash value was 1.42%. The degree of reaction completion was thus 89.3%.

EXAMPLE 5

Sorbitol decanoate was prepared by adding 380.80 grams of sorbitol and 302.0 grams of decanoic acid to a one-liter round bottom flask. 27.14 grams of 75% phosphoric acid were added. The agitator was turned on and the temperature was set to 150° C. The total reaction time was seven hours and ten minutes. The phosphoric acid was neutralized with 22.83 grams of calcium hydroxide and the solution was filtered to remove the calcium phosphate. The final product was analyzed and the free acid remaining was 7.50%. The density was 1.05 g/cc and the ash value was 1.00%. The degree of reaction completion was thus 76.0%.

EXAMPLE 6

Xylitol laurate was prepared by adding 466.8 grams of xylitol to 420.0 grams of lauric acid in a two liter round bottom flask. A mechanical stirrer, heating mantle and temperature controller were attached. Phosphoric acid was used as the catalyst and 35.25 grams of 75% acid was added. The temperature was set to 150° C. and the total reaction time was nine hours. At the end of nine hours the phosphoric acid was neutralized with 29.65 grams of calcium hydroxide and the solution was filtered to remove the calcium phosphate that formed upon neutralization. The xylitol laurate was analyzed and had 11.0% free acid remaining and the ash value was only 0.60%. The degree of reaction completion was thus 77.5%.

EXAMPLE 7

Sorbitol laurate was prepared in a similar manner as xylitol laurate. In this case, 600.76 grams of lauric acid and 776.01 grams of sorbitol were added to a round bottom flask. Phosphoric acid was used as the catalyst and 54.73 grams of 75% acid was added. A mechanical stirrer was used to provide the agitation and a heating mantle and temperature controller were used to control the temperature. The temperature of the reaction was set at 160° C. The reaction was stopped after 29.5 hours and the free fatty acid was high at 12.0%. The solution was neutralized with calcium hydroxide and filtered to remove the calcium phosphate precipitate. No other analysis was done on this product. The degree of reaction completion was thus 73.2%.

EXAMPLE 8

Xylitol decanoate was prepared. 602.5 grams of xylitol were placed in a two liter round bottom flask with a mechanical stirrer and heating mantle and temperature controller attached. 517.08 grams of decanoic acid were added to the flask. Phosphoric acid was used as the catalyst and 44.52 grams of 75% phosphoric acid was added. The reaction proceeded for 13 hours and 30 minutes. At the end of the reaction the phosphoric acid was neutralized with calcium hydroxide and the solution was filtered to remove the calcium phosphate precipitates. The free acid was measured and the value was 6.9%. The degree of reaction completion was thus 85.7%.

We claim:

1. A method for treating plants to reduce or eliminate insect pests utilizing monoester of an organic acid with a five to twelve carbon polyol consisting essentially of high monoester concentration obtained by the process comprising:

(a) selecting an organic acid with six to twelve carbons;

(b) selecting a polyol with five to twelve carbons;

(c) by reacting said polyol by esterification with the organic acid or transesterification with the organic acid ester, (d) by adding said polyol in a quantity that produces a monoester stoichiometrically plus approximately an additional 10%;

(e) adding an esterification or transesterification catalyst;

(f) maintaining said temperature and pressure in said reactor to remove water until reaction is essentially complete;

(g) neutralizing solution with a base and bringing said solution to desired pH; and (h) filtering said solution to remove solid particles; wherein:

the monoester is sucrose octanoate, sorbitol octanoate, sorbitol decanoate, xylitol decanoate, or xylitol laurate.

* * * * *